United States Patent [19]

Aufdembrink et al.

[11] Patent Number: 5,043,508

[45] Date of Patent: * Aug. 27, 1991

[54] PROCESS FOR PREPARING LONG CHAIN ALKYL AROMATIC COMPOUNDS

[75] Inventors: Brent A. Aufdembrink, Wilmington, Del.; Charles T. Kresge, West Chester, Pa.; Quang N. Le, Cherry Hill, N.J.; Joosup Shim, Wenonah, N.J.; Stephen S. Wong, Medford, N.J.

[73] Assignee: Mobil Oil Corporation, Fairfax, Va.

[ * ] Notice: The portion of the term of this patent subsequent to Mar. 27, 2007 has been disclaimed.

[21] Appl. No.: 483,690

[22] Filed: Feb. 23, 1990

Related U.S. Application Data

[63] Continuation-in-part of Ser. No. 358,105, May 30, 1989, Pat. No. 4,912,277.

[51] Int. Cl.$^5$ .................. C07C 2/64; C07C 15/107
[52] U.S. Cl. ..................... 585/455; 585/467
[58] Field of Search ................... 585/455, 467

[56] References Cited

U.S. PATENT DOCUMENTS

| | | | |
|---|---|---|---|
| 3,251,897 | 5/1966 | Wise | 260/671 |
| 3,751,504 | 8/1973 | Keown et al. | 260/672 |
| 4,211,665 | 7/1980 | Pellegrini, Jr. | 252/63 |
| 4,238,343 | 12/1980 | Pellegrini, Jr. | 585/24 |
| 4,301,316 | 11/1981 | Young | 585/455 |
| 4,301,317 | 11/1981 | Young | 585/455 |
| 4,600,503 | 7/1986 | Angevine et al. | 208/251 |
| 4,604,491 | 8/1986 | Dressler et al. | 585/26 |
| 4,714,794 | 12/1987 | Yoshida et al. | 585/26 |
| 4,831,005 | 5/1989 | Aufdembrink | 502/242 |
| 4,831,006 | 5/1989 | Aufdembrink | 502/242 |
| 4,912,277 | 3/1990 | Aufdembrink et al. | 585/467 |

FOREIGN PATENT DOCUMENTS 0205711 12/1986 European Pat. Off. .
WO8800090 1/1988 PCT Int'l Appl. .

OTHER PUBLICATIONS

A. F. Reid et al., "A New Class of Compounds", Acta Cryst (1963), B24, 1228.
W. A. England et al., "Ion Exchange in the $Cs_x$ [$Ti_{2-X}2MgX_2$]O Structure", Journal of Solid State Chemistry 49, 300–308 (1983).
I. E. Grey et al., "The Stability and Structure of $Cs_x[Ti_{2-x/4} x/4]O_4$, 0.61 x O Journal of Solid State Chemistry", 66, 7–19 (1987).
B. L. Shapiro, "Heterogenous Catalysis", IUCCP Meeting at Texas A&M, pp. 71–94, Apr. 1–4, 1984.
T. Jin, T. Yamaguchi and K. Tanabe, "Mechanism of Acidity Generation on Sulfur–Promoted Metal Oxides", J. Phys. Chem., 90, 4796–4796, 1986.

*Primary Examiner*—Patrick P. Garvin
*Assistant Examiner*—E. D. Irzinski
*Attorney, Agent, or Firm*—Alexander J. McKillop; Charles J. Speciale; Edward F. Kenehan, Jr.

[57] ABSTRACT

Relatively long chain alkyl aromatic compounds are prepared by alkylating an alkylatable aromatic compound with a relatively long chain alkylating agent under alkylation reaction conditions in the presence of a layered material as an alkylation catalyst. The layered material contains titanate in the layers and oxide pillars separating the layers. The layers also contain vacancies and/or metals incorporated therein. The degree of alkylation is a function of the interplanar d-spacing of the pillared material, which is, in turn a function of the chain length of the swelling agent used to prepare the layered material.

8 Claims, No Drawings

PROCESS FOR PREPARING LONG CHAIN ALKYL AROMATIC COMPOUNDS

CROSS REFERENCE TO RELATED APPLICATIONS

This application is a continuation-in-part of copending U.S. application Ser. No. 358,105, filed May 30, 1989, now U.S. Pat. No. 4,912,277. This application is also related to copending U.S. application Ser. No. 358,231, filed May 30, 1989. The entire disclosures of these applications are expressly incorporated herein by reference.

BACKGROUND

This application relates to a process for preparing long chain alkyl aromatic compounds by alkylating an aromatic compound with a relatively long chain alkylating agent employing a layered material as alkylation catalyst.

The alkylation of aromatic hydrocarbons with an olefin in the presence of a zeolite having uniform pore openings of from about 6 to about 15 Angstrom units is described in U.S. Pat. No. 2,904,607. U.S. Pat. No. 3,251,897 describes the alkylation of aromatic hydrocarbons in the presence of X- or Y-type zeolites, specifically such type zeolites wherein the cation is a rare earth metal species and/or hydrogen. U.S. Pat. Nos. 3,751,504 and 3,751,506 describe the vapor phase alkylation of aromatic hydrocarbons with olefins, e.g., benzene with ethylene, in the presence of a ZSM-5 type zeolite catalyst.

U.S. Pat. Nos. 3,631,120 and 3,641,177 describe a liquid phase process for the alkylation of aromatic hydrocarbons with olefins in the presence of certain zeolites.

U.S. Pat. Nos. 4,301,316 and 4,301,317 disclose the use of such zeolites as ZSM-4, ZSM-20, ZSM-38, mazzite, Linde Type L and zeolite Beta to catalyze the alkylation of benzene with relatively long chain olefins to produce long chain alkylbenzenes.

Alkylation reactions may be carried out using well-known Friedel-Crafts catalysts such as $AlCl_3$, $AlBr_3$, $FeCl_3$, $SnCl_4$, $BF_3$, $ZnCl_2$, HF, $H_2SO_4$, $H_3PO_4$ as disclosed in U.S. Pat. Nos. 4,035,308; 4,691,068; 3,173,965 and 4,148,834. These Friedel-Crafts alkylation processes normally require additional processing steps including filtration, neutralization and washing to remove the catalyst.

U.S. Pat. Nos. 4,604,491 and 4,714,794, the entire disclosures of which are expressly incorporated herein by reference, suggest that alkylated naphthalenes containing certain long chain alkyl groups are useful as base stocks for various synthetic lubricating oil compositions.

SUMMARY

According to an aspect of this application, there is provided a process for making a synthetic base oil for functional fluids and greases, said method comprising contacting naphthalene with at least one alkylating agent possessing an alkylating aliphatic group having at least six carbon atoms under alkylation reaction conditions and in the presence of an alkylation catalyst to provide an alkylated naphthalene product possessing at least one alkyl group derived from said alkylating agent, said catalyst comprising a layered material comprising a layered metal oxide and pillars of an oxide of at least one element selected from Groups IB, IIB, IIIA, IIB, IVA, IVB, VA, VB, VIA, VIIA and VIIIA of the Periodic Table of the Elements separating the layers of the metal oxide, wherein each layer of the metal oxide has the general formula

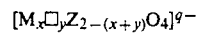

wherein M is at least one metal of valence n wherein n is n integer between 0 and 7, □ represents a vacancy site, Z is titanium, and wherein $q = 4y - x(n-4)$ $0 < x + y < 2$ wherein said layered material has an interplanar distance of greater than 10 Angstroms.

EMBODIMENTS

An aromatic compound may be alkylated with a relatively long chain alkylating agent to produce a long chain alkyl aromatic product employing as alkylation catalyst a layered material as described herein. These long chain alkylbenzenes are useful, inter alia, as intermediates in the manufacture of synthetic detergents. The alkylation of an aromatic hydrocarbon stream, e.g., one containing one or more of benzene, toluene, xylene, naphthalene, and the like, with a relatively long chain alkylating agent may also produce an aromatic lube base stock of low pour and cloud point, high viscosity and improved thermal and oxidative stability properties.

The term "aromatic" in reference to the alkylatable compounds which are useful herein is to be understood in accordance with its art-recognized scope which includes alkyl substituted and unsubstituted mono- and polynuclear compounds. Compounds of an aromatic character which posses a hereto atom are also useful provided they do not act as catalyst poisons under the reaction conditions selected.

Substituted aromatic compounds which can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups which do not interfere with the alkylation reaction.

Suitable aromatic hydrocarbons include benzene, naphthalene, anthracene, naphthacene, perylene, coronene and phenanthrene.

Generally, the alkyl groups which can be present as substituents on the aromatic compound contain from one to about 40 carbon atoms, e.g., from about one to eight carbon atoms, e.g., from about one to four carbon atoms.

Suitable alkyl substituted aromatic compounds include toluene, xylene, isopropylbenzene, normal propylbenzene, alpha-methylnaphthalene, ethylbenzene, cumene, mesitylene, durene, p-cymene, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene, 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methylphenanthrene. Higher molecular weight alkyl-aromatic hydrocarbons can also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecyltoluene etc. Very often alkylate is obtained as a high boiling fraction in which the alkyl group attached to the aromatic nucleus varies in size from about $C_6$ to about $C_{20}$.

Reformate containing substantial quantities of benzene, toluene and/or xylene constitutes a particularly useful feed for the alkylation process of this application.

The alkylating agents which are useful in the process of this application generally include any aliphatic or aromatic organic compound having one or more available alkylating aliphatic groups capable of reaction with the alkylatable aromatic compound. The alkylatable group itself should have at least about 6 carbon atoms, e.g., at least about 8, e.g., at least about 10 carbon atoms. Examples of suitable alkylating agents are olefins such as hexenes, heptenes, octenes, nonenes, decenes, undecenes, dodecenes, and the like; alcohols (inclusive of monoalcohols, dialcohols, trialcohols, etc.) such as hexanols, heptanols, octanols, nonanols, decanols, undecanols and dodecanols; and alkyl halides such as hexyl chlorides, octyl chlorides, dodecyl chlorides; and, higher homologs of the foregoing. Branched alkylating agents, especially oligomerized olefins such as the trimers, tetramers, pentamers, etc., of light olefins such as ethylene, propylene, the butylene, etc., or of heavier olefins such as octene, decene, dodecene, etc. are also useful herein.

The layered materials, which are used as an alkylation catalyst in processes described herein, are described in copending U.S. application Ser. No. 179,949, filed Feb. 25, 1988, as well as in PCT International Publication Number WO 88/00090, published Jan. 14, 1988. These layered materials comprise a layered metal oxide and pillars of an oxide of at least one element selected from Groups IB, IIB, IIIA, IIIB, IVA, IVB, VA, VB, VIA, VIIA and VIIIA of the Periodic Table of the Elements (Fisher Scientific Co. Cat. No. 5-702-10, 1978) separating the layers of the metal oxide, wherein each layer of the metal oxide has the general formula $$[M_x\square_yZ_{2-(x+y)}O_4]^{q-}$$

wherein M is at least one metal of valence n wherein n is an integer between 0 and 7 and preferably is 2 or 3, $\square$ represents a vacancy site, Z is a tetravalent metal, preferably titanium, and wherein $q=4y-x(n-4)$ and preferably is 0.6–0.9, $0<x+y<2$ This layered material may be prepared by a method which comprises the steps of starting with said layered metal oxide and physically separating the layers thereof by introducing an organic cationic species between the layers at interlayer anionic sites associated with the layered oxide, introducing between the separated layers of the layered oxide a compound capable of conversion to an oxide and then converting said compound to the oxide to form oxide pillars separating adjacent layers of the layered oxide.

It is to be appreciated that the term "layered" metal oxide is used herein in its commonly accepted sense to refer to a material which comprises a plurality of separate metal oxide layers which are capable of being physically displaced away from one another such that the spacing between adjacent layers is increased. Such displacement can be measured by X-ray diffraction techniques and/or by density measurements.

The present pillared oxide products may have relatively high interplanar distance (d-spacing), e.g., greater than about 6 Angstrom, e.g., greater than about 10 Angstrom, e.g., greater than 20 Angstrom up to and even exceeding 30 Angstrom. These materials are capable of being exposed to severe conditions such as those encountered in calcining, e.g., at temperatures of about 450° C. for about two or more hours, e.g., four hours, in nitrogen or air, without significant decrease, e.g., less than about 10%, in interlayer distance. Furthermore, such pillared oxides can be prepared without the severe dilution often necessary to introduce the interspathic material in prior art techniques of interlayering. Also, the size of interspathic oxide contained within the final product can be greatly varied because the oxide precursor species may be introduced in an electrically neutral form such that the amount of interspathic material incorporated within the layered titanometallate is not dependent upon the charge density of the original layered oxide. Charge density should be taken into consideration in determining the suitability of the cationic species introduced between the layers in the procedure used to prop open the layers prior to pillaring.

The present layered material may be made from a titanometallate starting material which contains anionic sites having interspathic cations associated therewith. Such interspathic cations may include hydrogen ion, hydronium ion and alkali metal cation.

More specifically, the present invention employs a layered metal oxide starting material in which each layer has the general formula $$[M_x\square_yZ_{2-(x+y)}O_4]^{q-}$$

wherein M is at least one metal of valence n wherein n is an integer between 0 and 7 and preferably is 2 or 3, represents a vacancy site, Z is a tetravalent metal, preferably titanium, and wherein $q=4y-x(n-4)$ and preferably is 0.6–0.9, $0<x+y<2$ Interposed between the layers of the oxide will be charge-balancing cations A of charge m wherein m is an integer between 1 and 3, preferably 1. Preferably A is a large alkali metal cation selected from the group consisting of Cs, Rb and K and M is a divalent or trivalent metal cation selected from at least one Mg, Sc, Mn, Fe, Cr, Ni, Cu, Zn, In, Ga and Al. For example, M can be both In and Ga. Structurally, these metal oxides consist of layers of $(M_x\square_yZ_{1-x-y})O_6$ octahedra which are trans edge-shared in one dimension and cis edge-shared in the second dimension forming double octahedral layers which are separated by the A cations in the third dimension. When Z is titanium, these materials can be prepared by high temperature fusion of a mixture of 1)

metal oxide, 2) alkali metal carbonate or nitrate and 3) titanium dioxide; or by fusion of a mixture of alkali metallate and titanium dioxide. Such fusion can be carried out in air in ceramic crucibles at temperatures ranging between 600° to 1100° C. after the reagents have been ground to an homogeneous mixture. The resulting product is ground to 20 to 250 mesh, preferably about 100 mesh, prior to the organic swelling and polymeric oxide intercalation steps.

Further description of the layered titanometallate starting materials and their methods of preparation can be found in the following references:

Reid, A. F.; Mumme, W. G.; Wadsley, A. D. *Acta Cryst.* (1968), B24, 1228; Groult, D.; Mercy, C.; Raveau, B. *J. Solid State Chem.* 1980, 32 289; England, W. A.; Burkett, J. E.; Goodenough; J. B., Wiseman, P. J. *J. Solid State Chem.* 1983, 49 300.

Use of these layered metal oxides as a layered starting material permits inclusion of different metal atoms into the layered starting material being treated which allows potential catalytically active sites to be incorporated in the stable layer itself. Moreover, variable amounts of metal atoms may be added to provide a catalyst with optimum activity for a particular process. Furthermore, the infinite trans-edge shared layer structure of the titanometallates instead of the sheared 3-block structure of, for example, $Na_2Ti_3O_7$ may reduce or eliminate shearing of the layers as a possible mechanism for thermal or hydrothermal decomposition of the calcined intercalated material. The variable charge density on the oxide layer, possible for these layered metal oxides due to the various oxidation states of metal oxides, the incorporated metal atom and the varying stoichiometry of the materials, may allow variation in the amount of the organic cationic species which can be exchanged into the material. This variation, in turn, permits variation of the ultimate concentration of the oxide pillars between the layers of the final product.

The layered metal oxide starting material may be initially treated with a "propping" agent comprising a source of organic cation, such as organoammonium cation, in order to effect an exchange of the interspathic cations resulting in the layers of the starting material being propped apart. Suitable organoammonium cations include such as n-dodecylammonium, n-octylammonium, n-heptylammonium, n-hexylammonium, n-butylammonium and n-propylammonium. During this propping or swelling step it is important to maintain a low hydrogen ion concentration to prevent decomposition of the titanometallate structure as well as to prevent preferential sorption of hydrogen ion over the propping agent. A pH range of 6 to 10, preferably 7 to 8.5 is generally employed during treatment with the propping agent. After this treatment, it has been found advantageous to wash out excess propping agent using propping agent-soluble reagent followed by washing with water. For example, ethanol is soluble in and hence suitable for use with an n-octylamine propping agent. Such washing permits greater incorporation of the oxide pillar precursor in the layered metal oxide. The water treatment allows penetration of water into the interlayer spaces which assists in subsequent hydrolysis the oxide pillar precursor.

The foregoing treatment results in the formation of a layered metal oxide of enhanced interlayer separation depending upon the size of the organic cation introduced. In one embodiment, a series of organic cation exchanges can be carried out. For example, an organic cation may be exchanged with an organic cation of greater size, thus increasing the interlayer separation in a step-wise fashion. Preferably, contact of the layered oxide with the propping agent is conducted in aqueous medium so that water is trapped between the layers of the "propped" species.

After the ion exchange, the organic-"propped" species may be treated with a compound capable of conversion, preferably by hydrolysis, to pillars of an oxide, preferably to a polymeric oxide. Where the treatment involves hydrolysis, this treatment may be carried out using the water already present in organic-"propped" material. In this case, the extent of hydrolysis may be modified by varying the extent to which the organic-"propped" species is dried prior to addition of the polymeric oxide precursor.

It is preferred that the organic cation deposited between the layers be capable of being removed from the pillared material without substantial disturbance or removal of the interspathic polymeric oxide. For example, organic cations such as n-octylammonium may be removed by exposure to elevated temperatures, e.g., calcination, in nitrogen or air, or by chemical oxidation preferably after the interspathic polymeric oxide precursor has been converted to the polymeric oxide pillars in order to form the layered product.

These layered products, especially when calcined, exhibit high surface area, e.g., greater than 200, 300, 400 or even 600 $m^2/g$, and thermal and hydrothermal stability making them highly useful as catalysts or catalytic supports, for hydrocarbon conversion processes, for example, alkylation.

The layered metal oxide starting material may be initially subjected to a swelling or propping step in which the material is treated with an organic compound capable of forming cationic species such as organophosphonium or organoammonium ion, between the oxide layers. Insertion of the organic cation between the adjoining layers serves to physically separate the layers in such a way as to make the layered material receptive to the interlayer addition of an electrically neutral, hydrolyzable, polymeric oxide precursor. In particular, alkylammonium cations have been found useful. Thus $C_3$ and larger alkylammonium, e.g., n-octylammonium, cations are readily incorporated within the interlayer spaces of the layered metal oxide serving to prop open the layers in such a way as to allow incorporation of the polymeric oxide precursor. The extent of the interlayer spacing can be controlled by the size of the organoammonium ion employed so that use of the n-propylammonium cation can achieve a interlayer spacing of 2 to 5 Angstrom whereas to achieve an interlayer spacing of 10 to 20 Angstrom an n-octylammonium cation or a cation of equivalent length is required. Indeed, the size and shape of the organic cation can affect whether or not it can be incorporated within the layered structure at all. For example, bulky cations such as tetrapropylammonium are generally undesirable for use while n-alkyl ammonium cations such as those derived from n-alkyl primary amines and $R_3R'N^+$ cations where R is methyl or ethyl and R is an n-alkyl group with at least 5 carbon atoms, are preferred. Preferably treatment with the organic cationic species is conducted in aqueous media so that water is then available to hydrolyze the electrically neutral, hydrolyzable polymeric oxide precursor subsequently introduced into the "propped" product.

Interspathic oxide pillars are then formed between the layers of the propped or swollen metal oxide starting material and may include an oxide, preferably a polymeric oxide, of zirconium or titanium or more preferably of an element selected from Group IVB of the Periodic Table (Fischer Scientific Company Cat. No. 5-702-10, 1978), other than carbon, i.e., silicon, germanium, tin and lead. Other suitable oxides include those of Group VA, e.g., V, Nb, and Ta, those of Group IIA, e.g., Mg or those of Group IIIB, e.g., B. Most preferably, the pillars include polymeric silica. In addition, the oxide pillars may include an element which provides catalytically active acid sites in the pillars, preferably aluminum.

The oxide pillars are formed from a precursor material which is preferably introduced between the layers of the organic "propped" species as a cationic, or more preferably, electrically neutral, hydrolyzable compound of the desired elements, e.g., those of Group IVB. The precursor material is preferably an organometallic compound which is a liquid under ambient conditions. In particular, hydrolyzable compounds, e.g., alkoxides, of the desired elements of the pillars are utilized as the precursors. Suitable polymeric silica precursor materials include tetraalkylsilicates, e.g., tetrapropylorthosilicate, tetramethylorthosilicate and, most preferably, tetraethylorthosilicate. Where the pillars also include polymeric alumina, a hydrolyzable aluminum compound can be contacted with the organic "propped" species before, after or simultaneously with the contacting of the propped titanometallate with the silicon compound. Preferably, the hydrolyzable aluminum compound employed is an aluminum alkoxide, e.g., aluminum isopropoxide. If the pillars are to include titania, a hydrolyzable titanium compound such as titanium alkoxide, e.g., titanium isopropoxide, may be used. In addition, the oxide precursor may contain zeolite precursors such that exposure to conversion conditions results in the formation of interspathic zeolite material as at least part of the oxide pillars.

After hydrolysis to produce the oxide pillars and calcination to remove the organic propping agent, the final pillared product may contain residual exchangeable cations. Such residual cations in the layered material can be ion exchanged by known methods with other cationic species to provide or alter the catalytic activity of the pillared product. Suitable replacement cations include cesium, cerium, cobalt, nickel, copper, zinc, manganese, platinum, lanthanum, aluminum, ammonium, hydronium and mixtures thereof.

Particularly preferred procedures for intercalating the layered materials described herein with metal oxide pillars are described in copending U.S. application Ser. No. 314,611, filed Feb. 23, 1989, as well as in U.S. Pat. Nos. 4,831,005 and 4,831,006. The entire disclosures of these patents and this application are expressly incorporated herein by reference. U.S. Pat. No. 4,831,005 describes plural treatments with the pillar precursor. Ser. No. 314,611 describes the use of an inert atmosphere, such as nitrogen, to minimize the formation of extralaminar polymeric oxide during the contact with the pillar precursor. U.S. Pat. No. 4,831,006 describes the use of elevated temperatures during the formation of the pillar precursor.

The resulting pillared products exhibit thermal stability at temperatures of 500° C. or even higher as well as substantial sorption capacities (as much as 10 to 25 wt % for $H_2O$ and $C_6$ hydrocarbon). Silica-pillared products possess interlayer separations of greater than 12 A and surface areas greater than 250 $m^2/g$ when divalent metal atoms, e.g., Mg, Ni, Cu and Zn, are present as the metal M of the product. Silica-pillared products incorporating trivalent metal atoms, e.g., Sc, Mn, Fe, Cr, In, Ga and Al can possess interlayer separations of 6 to 15 A.

The layered material alkylation catalyst described herein can optionally be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be exchanged into the composition, impregnated therein or intimately physically admixed therewith. Such component can be impregnated in, or on, the layered material such as, for example, by, in the case of platinum, treating the layered material with a solution containing a platinum metal-containing ion. Thus, suitable platinum compounds for this purpose include chloroplatinic acid, platinous chloride and various compounds containing the platinum amine complex.

The layered material may be subjected to thermal treatment, e.g., to decompose organoammonium ions. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

Prior to its use in the alkylation process described herein, the layered material catalyst should be dehydrated, at least partially. This dehydration can be done by heating the crystal to a temperature in the range of from about 200° C. to about 595° C. in an atmosphere such as air, nitrogen, etc., and at atmospheric, subatmospheric or superatmospheric pressures for between about 30 minutes to about 48 hours. Dehydration can also be performed at room temperature merely by placing the layered material in a vacuum, but a longer time is required to obtain a sufficient amount of dehydration.

The layered material catalyst can be shaped into a wide variety of particle sizes. Generally speaking, the particles can be in the form of a powder, a granule, or a molded product such as an extrudate having a particle size sufficient to pass through a 2 mesh (Tyler) screen and be retained on a 400 mesh (Tyler) screen. In cases where the catalyst is molded, such as by extrusion, the layered material can be extruded before drying or partially dried and then extruded.

It may be desired to incorporate the layered material with another material which is resistant to the temperatures and other conditions employed in the alkylation process described herein. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with layered material, i.e., combined therewith or present during its synthesis, which itself is catalytically active may change the conversion and/or selectivity of the catalyst. Inactive materials suitably serve as diluents to control the amount of conversion so that alkylation products can be obtained economically and orderly without employing other means for controlling the rate of reaction. These materials may be incorporated into naturally occurring clays, e.g., bentonite and kaolin, to improve the crush strength of the catalyst under commercial alkylation operating conditions. Said materials, i.e., clays, oxides, etc., function as binders for the catalyst. It is desirable to provide a catalyst having good crush strength because in commercial use, it is desirable to prevent the catalyst from breaking down into powder-like materials. These clay binders have been employed normally only for the purpose of improving the crush strength of the catalyst.

Naturally occurring clays which can be composited with layered materials include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with layered materials also include inorganic oxides, notably alumina.

In addition to the foregoing materials, the layered materials can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

The relative proportions of finely divided layered materials and inorganic oxide matrix vary widely, with the layered material content ranging from about 1 to about 90 percent by weight and more usually, particuarly when the composite is prepared in the form of beads, in the range of about 2 to about 80 weight of the composite.

The alkylation process described herein may be conducted such that the organic reactants, i.e., the alkylatable aromatic compound and the alkylating agent, are brought into contact with the layered material catalyst composition in a suitable reaction zone such as, for example, in a flow reactor containing a fixed bed of the catalyst composition, under effective alkylation conditions. Such conditions include a temperature of from about 0° C. to about 500° C., a pressure of from about 0.2 to about 250 atmospheres, a feed weight hourly space velocity (WHSV) of from about 0.1 to about 500 and an alkylatable aromatic compound to alkylating agent mole ratio of from about 0.1:1 to about 50:1. The WHSV is based upon the weight of the catalyst composition employed, i.e., the total weight of active catalyst (and binder if present). Preferred reaction conditions include a temperature within the approximate range of from about 100° C. to about 350° C., a pressure of from about 1 to about 25 atmospheres, a WHSV of from about 0.5 to about 100 and an alkylatable aromatic compound to alkylating agent mole ratio of from about 0.5:1 to about 5:1. The reactants can be in either the vapor phase or the liquid and can be neat, i.e., free from international admixture or dilution with other material, or they can be brought into contact with the layered material catalyst composition with the aid of carrier gasses or diluents such as, for example, hydrogen or nitrogen.

The alkylation process described herein can be carried out as a batch-type, semi-continuous or continuous operation utilizing a fixed or moving bed catalyst system. A preferred embodiment entails use of a catalyst zone wherein the hydrocarbon charge is passed concurrently or countercurrently through a moving bed of particle-form catalyst. The latter, after use, is conducted to a regeneration zone where coke is burned from the catalyst in an oxygen-containing atmosphere (such as air) at elevated temperature, after which the regenerated catalyst is recycled to the conversion zone for further contact with the organic reactants.

The alkylation activity of the layered material catalysts may be increased by treating these layered materials with aqueous solutions of sulfate compounds, such as aqueous sulfuric acid. The effect of sulfate promotion on the generation of strong acidity on metal oxides such as $ZrO_2$, $TiO_2$, $Fe_2O_3$, etc., has been observed by K. Tanabe as reported in "Heterogenous Catalysis", IUCCP Meeting at Texas A & M, Apr. 1-4, 1984, B. L. Shapiro (Editor), pp. 71-94, and by T. Jin, T. Yamaguchi and K. Tanabe as reported in J. Phys. Chem., 90, 4794-4796, 1986. Further sulfate treatments for increasing the alkylation activity of the present layered material catalysts are described in the aforementioned U.S. application Ser. No. 358,231, filed May 30, 1989.

In the Examples which follow, whenever sorption data are set forth for comparison of sorptive capacities for water, cyclohexane and/or n-hexane, they were equilibrium adsorption values determined as follows:

A weighed sample of the calcined adsorbent was contacted with the desired pure adsorbate vapor in an adsorption chamber, evacuated to less than 1 mm and contacted with 21 Torr of water vapor and 40 Torr of n-hexane or cyclohexane vapor, pressures less than the vapor-liquid equilibrium pressure of the respective adsorbate at 90° C. The pressure was kept constant (within about ±0.5 mm) by addition of adsorbate vapor controlled by a manostat during the adsorption period, which did not exceed about 8 hours. As adsorbate was adsorbed by the layered material, the decrease in pressure caused the manostat to open a valve which admitted more adsorbate vapor to the chamber to restore the above control pressures. Sorption was complete when the pressure change was not sufficient to activate the manostat. The increase in weight was calcuated as the adsorption capacity of the sample in g/100 of calcined adsorbant.

EXAMPLE 1

This Example describes the preparation of a layered material catalyst. $Cs_2CO_3$ (621g) and $TiO_2$ (795g) were fired at 650° C. three times, with intermediate grindings between firings. The fired material was ball-milled for 4 hrs (30% solids in $H_2O$), then exchanged with 1 M $NH_4NO_3$ (10 ml $NH_4NO_3$/g solid) at reflux until the Cs content was less than 200 ppm. After each exchange the sample was filtered and washed with 2 l hot water. The ammonium exchanged solid was swollen by refluxing in neat octylamine for 24 hrs. using a Dean-Stark trap in the condensation column to remove water from the system. The swollen solid was filtered and washed with 2000 ml EtOH, then air dried. This solid was treated with tetraethylorthosilicate (5 g TEOS/g solid) under nitrogen at 80° C. for 20 hrs, filtered and dried under nitrogen. The sample was then stirred in $H_2O$ for 6 hours at room temperature. The TEOS/$H_2O$ treatment was repeated once. The pillared material was obtained by calcining the dried TEOS treated material in flowing air at 500° C. for 240 minutes. Chemical and physical properties of the catalyst are summarized in Table 1.

TABLE 1

| | |
|---|---|
| Cs, ppm | 23 |
| Ti, wt % | 29.0 |
| $SiO_2$, wt % | 44.9 |
| Ash, wt % (1000° C.) | 97.52 |
| Surface Area, $m^2/g$ | 526 |
| Sorption wt % | |
| $H_2O$ | 22.7 |
| $n-C_6$ | 14.3 |
| cyclohexane | 15.7 |
| Density, g/cc | |
| Real | 2.799 |
| Particle | 0.83 |

EXAMPLE 2

This Example illustrates the catalytic activity of the catalyst prepared from Example 1 for alkylating benzene with the long chain alpha olefin, alpha tetradecene, a C-14 olefin. The alkylation reaction was carried out in a 1 liter autoclave. The conditions were 250 g of alpha C-14 olefin (Shell Neodene-14) and 50 g of benzene (2:1 mole ratio of olefin and benzene) with 23.7 g of Example 1 catalyst at 400° F. for 6 hours under nitrogen pressure of 400 psig. After decanting and filtering the catalyst, the total liquid product was then vacuum distilled at 650° F. to obtain a 63 wt % lube range material with the following properties:

| | |
|---|---|
| Pour point, °F. | −50 |
| Cloud point, °F. | −44 |
| KV @ 40° C., cSt | 21.41 |
| KV @ 100° C., cSt | 4.521 |
| VI | 127 |

EXAMPLE 3

In this Example, the alkylation of benzene with alpha C-14 olefin was carried out under identical process conditions as in Example 2 but using a conventional USY catalyst. The USY catalyst also promotes the alkylation reaction, but has a very low catalyst activity, providing only 14 wt % lube yield (see Table 2).

EXAMPLE 4

In this Example, ZSM-12 catalyst, an "intermediate" pore zeolite, was used in the C-14/benzene alkylation reaction. Similar to the result obtained with the USY catalyst as shown in Example 3, the ZSM-12 is not very active and provides only 22 wt % alkyl-benzene lube yield.

Table 2 compares the lube yield and lube properties produced from Example 1 catalyst with USY and ZSM-12 catalysts:

TABLE 2

| | Example 2 | Example 3 | Example 4 |
|---|---|---|---|
| Catalyst | Example 1 | USY | ZSM-12 |
| Lube yield, wt % | 63.0 | 14.0 | 11.0 |
| Lube Properties | | | |
| Pour Point, °F. | −50 | −35 | −40 |
| Cloud Point, °F. | −44 | −32 | −24 |
| KV @ 40° C., cSt | 21.41 | 15.10 | 14.39 |
| KV @ 100° C., cSt | 4.521 | 3.626 | 3.547 |
| VI | 127 | 126 | 130 |

The Example 1 layered material catalyst is much more active and produces alkylated benzene lube base stock with lower pour and cloud point than either USY or ZSM-12 catalysts.

EXAMPLE 5

This Example illustrates the excellent alkylation activity of the Example 1 catalyst when naphthalene is substituted for the benzene of Example 2. The reaction was carried out under process conditions identical to those used in Example 2 using a 2:1 mole ratio of alpha C-14 and naphthalene. The alkylated naphthalene lube yield is about 91 wt %. This synthetic lubricant contains predominantly a mixture of mono-, di- and tri-alkyl naphthalenes and has following properties:

EXAMPLE 5

| | |
|---|---|
| Lube yield, wt % | 91 |
| Pour Point, °F. | −65 |
| KV @ 40° C., cSt | 66.13 |
| KV @ 100° C., cSt | 8.700 |
| VI | 104 |

EXAMPLE 6

This Example describes a sulfate treatment of the Example 1 catalyst. The Example 1 catalyst (20 g) was stirred in 500 ml of 1N $H_2SO_4$ for 10 minutes, filtered and air dried to yield 22.39 g of sulfate-containing material. The solid was dried at 120° C. for 2 hrs. (22.3 g yield), then calcined at 500° C. for 60 minutes to produce 19.0 g of sulfated treated catalyst.

EXAMPLE 7

Under experimental conditions identical to those used in Example 2, sulfate-containing Example 1 catalyst prepared in Example 6 is more active for the alkylation reaction and provides about 92 wt % lube yield as compared to 63 wt % without sulfate treatment. The properties of alkylated benzene lubes produced from the layered material catalyst with and without sulfate promotion are shown as follows:

| | Example 2 | Example 7 |
|---|---|---|
| Catalyst | Ex. 1 | Ex. 6 |
| Sulfate Treatment | No | Yes |
| S on Catalyst, wt % | — | 1.22 |
| Surface Area, $m^2/g$ | 526 | 327 |
| Lube Yield, wt % | 63 | 92 |
| Lube Properties | | |
| Pour point, °F. | −50 | −50 |
| Cloud point, °F. | −44 | −50 |
| KV @ 40° C., cSt | 21.41 | 23.70 |
| KV @ 100° C., cSt | 4.521 | 4.826 |
| VI | 127 | 128 |

The GC and FIMS analysis together with H- and C-NMR measurement indicate that these synthetic lubricants comprise mainly a mixture of mono-, di- and tri-alkyl benzenes with the C-14 alkyl chain length. To much lesser extent, the layered material catalysts also promote oligomerization reactions under these process conditions. Lowering a olefin: benzene ratio to less than 2 would eliminate or reduce the oligomerization reaction. These alkylbenzene lubricants have excellent low temperature viscometric properties as indicated by very low pour and cloud points (−45° F.). They may find wide temperature range applications because of their high VI of 127 -128.

Further Examples of sulfate treatments are provided as Examples 8-10 of the aforementioned U.S. application Ser. No. 358,231.

EXAMPLE 8

This Example demonstrates that product selectivity of aromatic alkylation reactions can be altered by utilizing pillard layered catalysts with varying interlayer separation. When utilized for the demonstrated case of alkylation of naphthalene with $C_{14}$ alpha olefins, the degree of alkylation can be controlled, producing potential lube base stocks with varying physical properties.

Lube product quality is closely associated with the molecular structure of the constituent molecules (i.e., short vs long chain paraffins; branched vs normal chain paraffins). Alkylated aromatics have been identified as candidates for lube basestocks needing stability towards oxidation during use. The degree of alkylation of the aromatics may be one mechanism that lube product qualities can be varied. When prepared by catalytic alkylation of aromatic moieties, the degree of alkylation might be excepted to be limited by the size of the pore in the catalyst during preparation. The pillared vacancy titanometallate catalyst, described here, are unique in that similar catalytic sites associated with the layer are present in materials where the pore sizes have been varied in a regular fashion. This Example demonstrates that the degree of alkylation (i.e., product selectivity) can be determined by selecting a catalyst with appropriate pore opening. The utility of widely variable pore size is not possible with conventional zeolite catalysts.

The preparation of an octylamine swollen pillared vacancy containing titanate has been previously described herein in Example 1. Four different materials were prepared similarly, except that four different alkylamines were used as swelling agents [butylamine ($C_4$), hexylamine ($C_6$), octylamine ($C_8$), and dodecylamine ($C_{12}$)], differing only in the dimension of the organic chain. The $C_{12}$ swollen material was prepared by first pre-swelling the ammonium titanate with butylamine, followed by further swelling with dodecylamine at 150° C. The dodecylamine swollen solid was treated twice with TEOS prior to the initial $H_2O$ treatment as described. Chemical and physical properties of the catalyst are shown in Table 3.

The materials were evaluated for catalytic activity in the alkylation of naphthalene with a $C_{14}$ alpha olefin, as described in Example 2. Conditions of the reaction are outlined in Table 4.

The results of the evaluation are shown in Table 5. The material swollen with the $C_4$ amine shows predominately mono-alkylated product with some di-alkylated product and to lesser extend some tri-alkylated product. As the d-spacing of the pillared catalyst increases, the product selectivity shifts to higher alkylated products at the expense of the lower alkylated products. Thus, greater amounts of di- and tri-alkylated products were observed for the $C_6$ swollen pillared material relative to the $C_4$ case. The $C_8$ case exhibited greatly increased proportion of tri-alkylated product relative to the $C_4$ and $C_6$ materials. The $C_{12}$ product selectivities show a significant shift towards the higher alkylated products. Relatively little mono-alkylated naphthalene is observed and the di- and tri-alkylated products predominate. Significantly, the formation of tetra-alkylated product is observed with the $C_{12}$-derived catalyst.

Furthermore, due to the large pore dimension (i.e., greater interlayer distance, see Table 5) which promotes the accessibility of the active sites, the $C_{12}$-derived catalyst showed an improved alkylation activity over other catalysts. It provides 91 wt % alkylated lube yield in comparison to 72 wt % from $C_8$-catalyst and 64 wt % from $C_4$− catalyst.

Lube product quality is closely associated with molecular structure. The ability to control the product selectivity by using particular catalysts provides the means to control product quality to obtain a product with optimum qualties.

Table 6 provides physical properties for the alkylated naphthalene lubricants produced. As shown by Table 6, the $C_{12}$-derived catalyst produced alkylated naphthalene lubricant with higher viscosity as well as higher viscosity index.

In a larger sense, this reaction demonstrates one facet of the desirability of pillared layered materials—the ability to control the pore size. In essence, knowing that the layered material is active as a catalyst for a particular reaction, one can then prepare the pillared material with the pore size which will produce the desired product selectivity.

TABLE 3

Properties of Various Cn Swollen Materials

| Swelling Agent | Ti wt % | SiO$_2$ wt % | % Ash | SA, m$^2$/g | d-Spacing (Å) | Static Adsorption Capacity H$_2$O wt % | c-C$_6$ wt % | n-C$_6$ wt % |
|---|---|---|---|---|---|---|---|---|
| C4 | 42.3 | 34.4 | 97.30 | 385 | 15.0 | 18.7 | 10.4 | 10.2 |
| C6 | 30.2 | 48.6 | 97.60 | 479 | 18.4 | 20.5 | 13.4 | 12.6 |
| C8 | 19.6 | 54.6 | 93.86 | 576 | 22.0 | 23.3 | 15.2 | 14.2 |
|  | 23.9 | 50.4 | 95.60 | 614 |  | 25.3 | 17.0 | 15.9 |
| C12 | 34.1 | 43.6 | 98.50 | 901 | 28.5 | 42.0 | 31.6 | 27.7 |

TABLE 4

Reaction Conditions

| | |
|---|---|
| Olefin:Naphthalene | 2:1 molar |
| Temperature | 400° F. |
| Time | 6 hrs |
| Pressure | 400 psig N$_2$ |

TABLE 5

Aromatic Alkylation

| Amine Carbons | C$_4$ | C$_6$ | C$_8$ | C$_{12}$ |
|---|---|---|---|---|
| Interlayer Separation (Å)* | 8.0 | 11.4 | 15.0 | 21.5 |
| Total Alkylated, wt % | 64 | 75 | 72 | 91 |
| Distribution, wt % | | | | |
| Mono- | 64 | 61 | 56 | 20 |
| Di- | 31 | 33 | 31 | 46 |
| Tri- | 5 | 6 | 13 | 31 |
| Tetra- | — | — | — | 6 |
| Conversion, wt % | | | | |
| Naphthalene | 79 | 92 | 88 | 96 |

TABLE 5-continued

| Aromatic Alkylation | | | | |
|---|---|---|---|---|
| Alpha-$C_{14}$ Olefin | 59 | 70 | 67 | 96 |

*Interlayer separation represents the free space between the layers. This is calculated by subtracting the layer thickness (7.0Å) from the d-spacing determined from x-ray diffraction.

TABLE 6

| Physical Properties of Alkylated Naphthalene | | | | |
|---|---|---|---|---|
| Amine Carbon No. | C4 | C6 | C8 | C12 |
| Pour Point, °F. | −60 | −50 | −55 | −35 |
| KV @ 40 C., cSt | 33.73 | 37.23 | 42.65 | 93.69 |
| KV @ 100 C., cSt | 5.48 | 6.29 | 6.88 | 11.35 |
| Viscosity Index | 96 | 97 | 101 | 108 |

What is claimed is:

1. A process for making a synthetic base oil for functional fluids and greases, said method comprising contacting naphthalene with at least one alkylating agent possessing an alkylating aliphatic group having at least six carbon atoms under alkylation reaction conditions and in the presence of an alkylation catalyst to provide an alkylated naphthalene product possessing at least one alkyl group derived from said alkylating agent, said catalyst comprising a layered material comprising a layered metal oxide and pillars of an oxide of at least one element selected from Groups IB, IIB, IIIA, IIIB, IVA, IVB, VA, VB, VIA, VIIA and VIIIA of the Periodic Table of the Elements separating the layers of the metal oxide, wherein each layer of the metal oxide has the general formula $$[M_x\square_yZ_{2-(x+y)}O_4]^{q-}$$

wherein M is at least one metal of valence n wherein n is an integer between 0 and 7, $\square$ represents a vacancy site, Z is titanium, and wherein $$q=4y-x(n-4)$$

$$0<x+y<2$$

wherein said layered material has an interplanar distance of greater than 10 Angstroms.

2. A process according to claim 1, wherein said layered material is prepared from a layered oxide swollen with an n-butylamine swelling agent.

3. A process according to claim 1, wherein said layered material is prepared from a layered oxide swollen with an n-hexylamine swelling agent.

4. A process according to claim 1, wherein said layered material is prepared from a layered oxide swollen with an n-octylamine swelling agent.

5. A process according to claim 1, wherein said layered material is prepared from a layered oxide swollen with an n-dodecylamine swelling agent.

6. A process according to claim 1, wherein said alkylating agent is an alpha olefin having 14 carbon atoms.

7. A process according to claim 4, wherein said alkylating agent is an alpha olefin having 14 carbon atoms.

8. A process according to claim 5, wherein said alkylating agent is an alpha olefin having 14 carbon atoms.

* * * * *